United States Patent [19]

Takahashi et al.

[11] Patent Number: 5,594,178
[45] Date of Patent: Jan. 14, 1997

[54] STRENGTH EVALUATION METHOD FOR BRITTLE MATERIAL PIECES

[75] Inventors: Hideo Takahashi, Yokohama; Shinji Tanaka, Funabashi; Hiroshi Maeno, Tokyo, all of Japan

[73] Assignee: Asahi Glass Company Ltd., Tokyo, Japan

[21] Appl. No.: 552,118

[22] Filed: Nov. 2, 1995

[30] Foreign Application Priority Data

Nov. 8, 1994 [JP] Japan .................................. 6-273554

[51] Int. Cl.⁶ ........................................................ G01N 3/32
[52] U.S. Cl. ............................................. 73/808; 73/813
[58] Field of Search ............................. 73/808, 809, 810, 73/811, 813, 814

[56] References Cited

U.S. PATENT DOCUMENTS

| | | | |
|---|---|---|---|
| 4,064,745 | 12/1977 | Gaddum | 73/808 |
| 4,090,401 | 5/1978 | Yammoto et al. | 73/808 |
| 4,696,581 | 9/1987 | Tsushima et al. | 384/565 |
| 5,073,178 | 12/1991 | Mimori et al. | |
| 5,349,870 | 9/1994 | Webber et al. | 73/808 |
| 5,476,009 | 12/1995 | Dimarogonas | 73/808 |

*Primary Examiner*—Hezron E. Williams
*Assistant Examiner*—Max H. Noori
*Attorney, Agent, or Firm*—Oblon, Spivak, McClelland, Maier & Neustadt, P.C.

[57] ABSTRACT

A strength evaluation method for evaluating the strength of brittle material pieces by applying momentary loading a plurality of times, the momentary loading momentarily applying a tensile stress to a brittle material piece; and gradually decreasing the peak load value of the subsequent momentary loading.

8 Claims, 7 Drawing Sheets

STRENGTH EVALUATION METHOD FOR BRITTLE MATERIAL PIECES

BACKGROUND OF THE INVENTION

1. Field of the Invention

The present invention relates to a strength evaluation method for brittle material pieces, in particular, a strength evaluation method for brittle material pieces which can accurately evaluate the strength of brittle material pieces such as ceramics and glass while, restraining pieces that passed a test from undergoing strength degradation, and eliminate pieces having low strength.

2. Discussion of Background

When brittle material pieces (including a product made from a brittle material) such as ceramics and glass are used under a high stress, a proof test has been carried out prior to use to see whether the brittle material pieces are fractured by application of a predetermined stress. In the proof test, brittle material pieces which have not been fractured are determined as survived pieces, and low strength pieces which have been fractured are eliminated as pieces that failed the test. However, because the stress is applied to the brittle material pieces in the proof test, the survived pieces which have not been fractured by the proof test include ones which have undergone strength degradation caused by accumulation of damage due to e.g. crack growth. To what extent such strength degradation causes varies depends on not only the kind of the brittle material but also the magnitude of the applied stress.

In general, it is considered that no plastic deformation causes in brittle materials, accumulation of damage at a crack tip is relatively small and no fracture is caused by gradually accumulating damage as a result of application of a stress, and that brittle materials have linear fracture behavior wherein elastic deformation continues until a certain limit stress is exerted, and immediate fracture causes at the instant when a stress exceeds the limit.

Since brittle materials have the linear fracture behavior, accumulation of damage in the survived pieces is relatively small and strength degradation is not susceptible in the proof test when a stress applied to a brittle material piece is fairly smaller than the material strength of the brittle material piece. However, when a high stress close to the material strength of the brittle material piece is applied, strength degradation is susceptible to cause.

For those reasons, a conventional strength evaluation method for brittle material pieces has eliminated only significantly low strength pieces as pieces that failed the test by carrying out a so-called proof test wherein a stress which is fairly lower than the average strength of a group of brittle material pieces is applied for a predetermined period of time and is released.

However, a product which is made from a brittle material is in some applications required to be used under several tens to over one hundred percent of the average strength. In such cases, it is necessary to evaluate the strength by applying to the product a stress close to the average strength. In the conventional strength evaluation method, the ratio of brittle material pieces which have fractured in the proof test increases, and that many pieces which have caused strength degradation are existing in pieces determined as the survived pieces.

Because most of conventional brittle material pieces which have been subjected to such a proof test are dense and substantially homogeneous structural material (e.g. mechanical parts), and have such outstanding linear fracture behavior, the conventional proof test is applicable. However, the linear fracture behavior is not applicable to a heterogeneous brittle material such as porous ceramics used in a filter of a filter apparatus, and a ceramics composite material with particles and fibers distributed in a ceramic matrix. Application of a stress in the test causes strength degradation in them, and even application of a smaller stress than the average strength causes strength degradation due to accumulation of damage. The conventional strength evaluation method has the problem in that a product which has caused strength degradation is existing in products determined as survived pieces.

This problem is significantly important because for example if only one filter tube is broken for some reason in a filter apparatus for a hot gas with a large number of porous ceramic filter tubes mounted thereto, a large system such as a power plant shuts down in the entirety.

SUMMARY OF THE INVENTION

It is an object of the present invention to provide a strength evaluation method for brittle material pieces capable of accurately evaluating and ensuring the strength of brittle material pieces by minimizing strength degradation in the brittle material pieces, in the light of the circumstances stated earlier.

The present invention is characterized in that a strength evaluation method for evaluating the strength of brittle material pieces by applying momentary loading a plurality of times, the momentary loading momentarily applying a tensile stress to a brittle material piece; and gradually decreasing the peak load value of the repeated momentary loading.

The strength degradation of a brittle material is normally caused by a tensile stress. According to the present invention, first of all, first momentary loading is carried out to momentarily apply a tensile stress to a brittle material piece to be subjected to strength evaluation. The peak load value of the stress at subsequent momentary loading is preferably set to a proof strength of the brittle material. Brittle material pieces which have no strength enough to resist the stress applied by the first momentary loading are fractured. In this manner, pieces that failed in a test can be eliminated. Momentary application of the stress causes little strength degradation in brittle material pieces which have strength enough to resist the tensile stress.

Next, second momentary loading is applied to the brittle material pieces which have not fractured by the first momentary loading. The peak load value of the second momentary loading is set to be smaller than that of the first momentary loading. The peak load value of the second momentary loading is preferably set to a tensile stress which corresponds to a desired fracture probability, e.g. fracture probability of 5%, based on a Weibull strength distribution. The Weibull strength distribution should be obtained by seeking in advance the strength distribution of a group of pieces of the same brittle material which have not fractured by the first momentary loading, and processing the sought strength distribution according to Weibull statistical analysis. A brittle material piece which has developed strength degradation by the first momentary loading to be unresistant to the tensile stress applied by the second momentary loading is fractured by the second momentary loading. As a result, when there is a piece which has caused strength degradation by the first momentary loading, such a piece can be surely eliminated. In addition, strength degradation in brittle material pieces can be minimized by carrying out subsequent momentary loading.

If there is a possibility that strength degradation can develop in the second momentary loading, third momentary loading is carried out having peak load value which is further smaller than the tensile stress of the second momentary loading. If necessary, subsequent momentary loading is applied in a similar manner. In order to provide a brittle material piece having more reliable proof strength, the peak load value of the tensile stress in subsequent momentary loading is set to a tensile stress which corresponds to desired fracture probability found based on a Weibull strength distribution. The Weibull strength distribution should be obtained by seeking in advance the strength distribution of a group of pieces of the same brittle material which have not fractured by the momentary loading just before, and processing the sought strength distribution according to Weibull statistical analysis.

If strength proof is required with high probability, constant stress loading is carried out at least one time next to the final momentary loading to apply for a predetermined period of time a tensile stress which has smaller value than the peak load value of the final momentary loading. Applying the constant stress loading can ensure to eliminate brittle material pieces which have caused strength degradation by the previous momentary loading.

The strength evaluation method according to the present invention is adequate for evaluating a brittle material which is susceptible to cause strength degradation by application of a tensile stress, such as a ceramics, a product made thereof, a composite material comprising a ceramic matrix and particles or fibers, a product made of such a composite material, glass, and a product made of glass. In particular, the method according to the present invention is appropriate as an evaluation method for a heterogeneous brittle material such as a ceramics and a product made thereof, and an evaluation method for a porous brittle material such as a filter tube made of a porous ceramics material. When such a brittle material is a tube, it is simple, reliable and effective to take a strength evaluation method wherein a hollow elastomer is arranged in the tube, and a fluid such as water is introduced into the hollow elastomer to expand the hollow elastomer so as to create an inner pressure, thereby applying a tensile stress to the tube in a circumferential direction.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1(A) and (B) are schematic views showing a three point bending strength test in accordance with an embodiment of the strength evaluation method of the present invention, FIG. 1(A) being a front view, and FIG. 1(B) being a side view;

DESCRIPTION OF THE PREFERRED EMBODIMENTS

Now, preferred embodiments of the strength evaluation method for a brittle material according to the present invention will be described in detail with reference to the accompanying drawings.

An example of a strength evaluation method for brittle material pieces according to the present invention is applied to a three point bending strength test commonly used as a testing method for brittle material pieces (including products made of a brittle material) such as ceramics will be explained. Three point bending strength tests do not exhibit the strength evaluation for the entirety of a brittle material piece because only a small volume of the piece is subjected to the maximum tensile stress applied. However, the strength evaluation method according to the present invention is applicable to the three point bending strength test as in a tensile test wherein a tensile stress is applied to the entirety of a brittle material piece.

Figure 1:
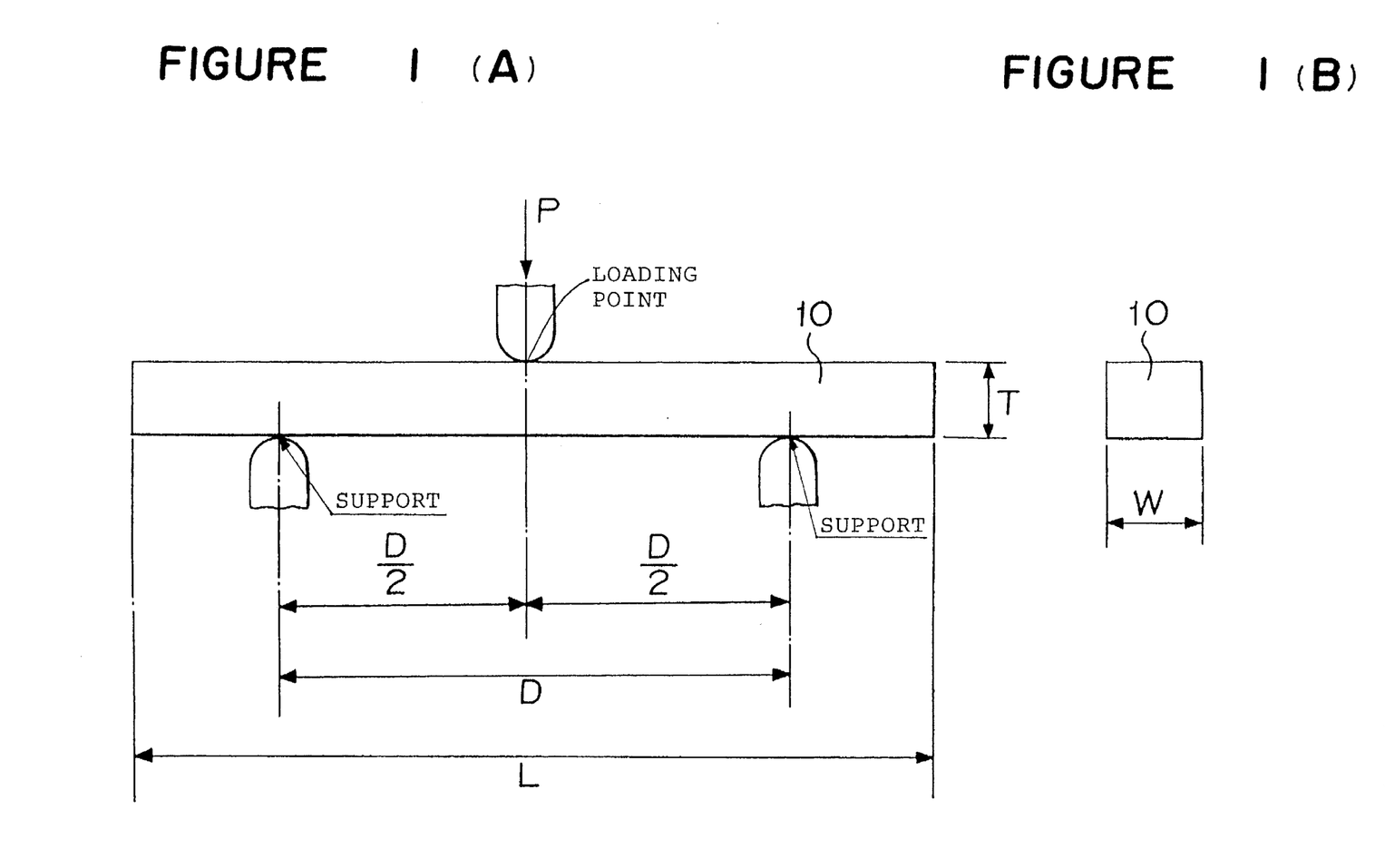

In FIGS. 1(A) and (B), there are shown schematic diagrams of the three point bending strength test. FIG. 1(A) is a front view, and FIG. 1(B) is a side view. In the bending test, test pieces 10 were cut from unused filter tubes (an outer diameter of 170 mm, an inner diameter of 140 mm) which were made from a porous cordierite ceramics and which had a thickness (T) of 11.5 mm, a width (W) of 20 mm and a length (L) of 50 mm, and a load was applied to the test pieces at the center of a span (D) of 40 mm. The filter tubes were mainly composed of dense cordierite aggregates which were obtained by crystallizing glass, and the filter tubes had been produced in accordance with the method disclosed in U.S. Pat. No. 5,073,187.

The position where a great tensile stress causes in the bending test lies in the vicinity of a surface opposite to the loading point of the test pieces 10.

Figure 2:
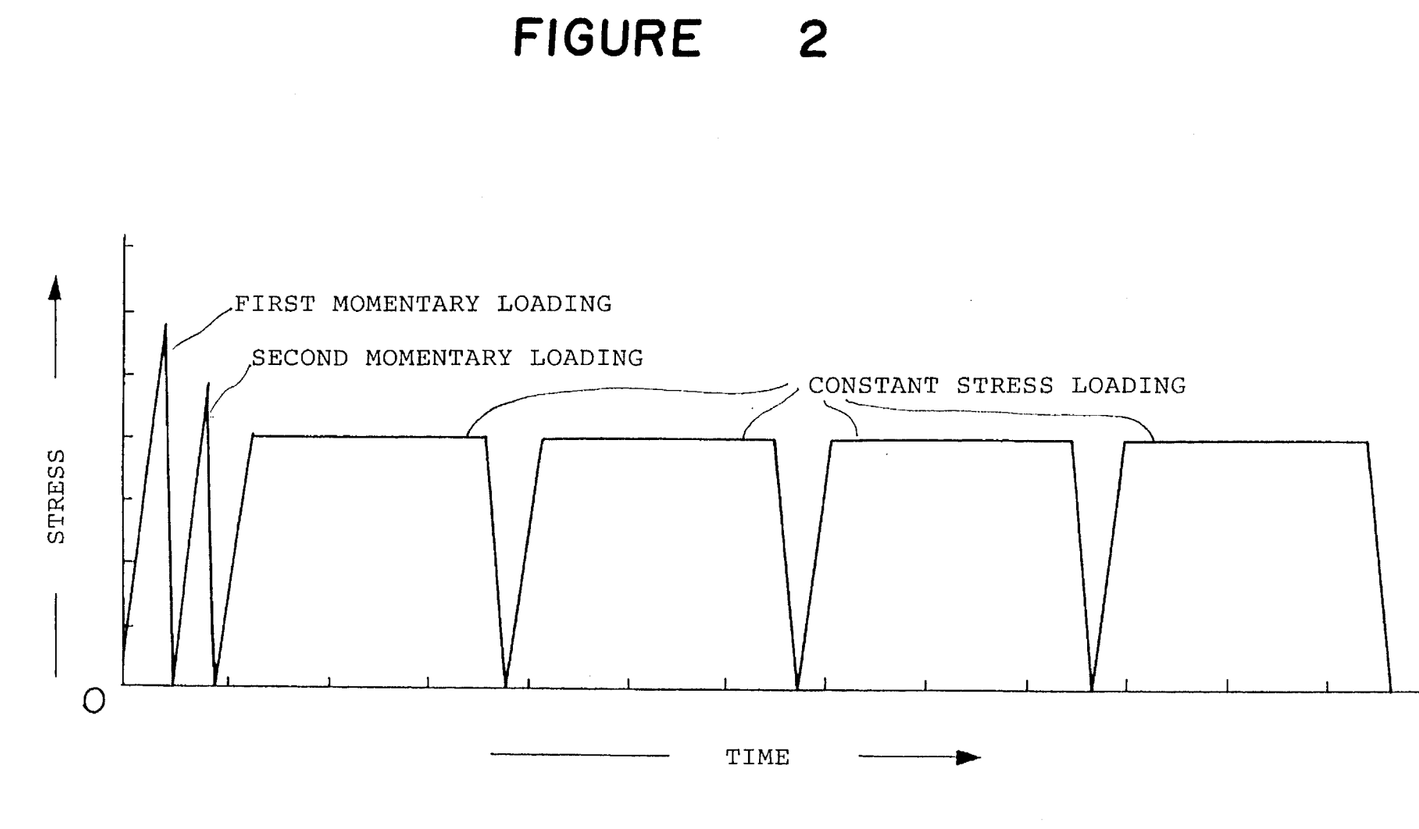
FIG. 2 is a stress application pattern diagram showing an example of the application pattern of a stress applied in an embodiment of the strength evaluation method for brittle material pieces of the present invention.

In FIG. 2, there is shown an example of the stress application pattern according to the strength evaluation method for brittle material pieces of the present invention in the bending test. As shown in FIG. 2, momentary loading which momentarily applied a bending stress to the test piece 10 was repeated two times, and constant stress loading lower than the final peak load value was repeated four times without pause after the second momentary loading. The stress application pattern in this example will be explained. In the first momentary loading, a stress which was 100% of the average initial strength of the test pieces 10 (42 pieces) (the relative stress is 1) was applied at a loading edge speed of 0.5 mm/min, and the loading was immediately released. As a result, failure occurred in about half of the test pieces.

Next, the second momentary loading was applied to test pieces which survived without failure in the first momentary loading. A bending stress wherein the peak load value corresponded to 85% of the average initial strength (the relative stress is 0.85) was applied at a loading edge speed of 0.5 mm/min, and the momentary loading was immediately released. In the first and second momentary loading, the bending stress was released immediately (brought to zero within 0.5 sec) after reaching the peak load value within 1 sec. Constant stress loading following the second momentary loading was applied to test pieces 10 which survived without being fractured in the second momentary loading. An operation wherein a constant stress load corresponding to 0.70 of the relative stress was applied for 2 min. was repeated four times. In order to see the strength distribution of the survived test pieces after the evaluation test, the strength of the survived test pieces 10 was measured by fracturing the test pieces at a loading edge speed of 0.5 mm/min.

Figure 4:
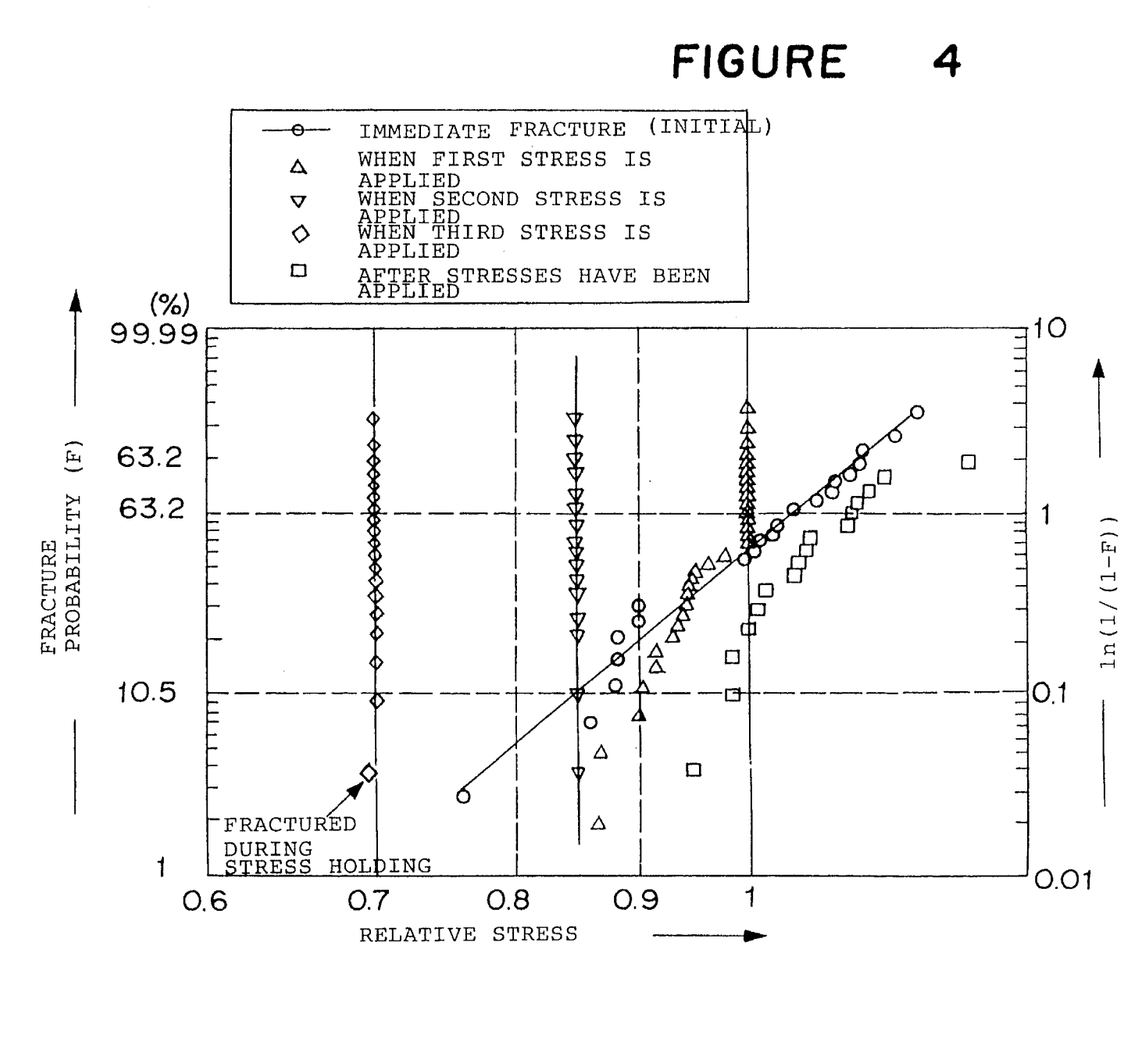
FIG. 4 is a Weibull strength distribution diagram of the fracture strength of brittle material pieces showing an example of the test results in accordance with the strength evaluation method for brittle material pieces of the present invention.

In FIG. 4, there is shown the test results by the strength evaluation method for a brittle material of the present invention. In FIG. 4, plots with a symbol "○" designate the initial Weibull strength distribution of a group of test pieces, and plots with a symbol "□" designate the Weibull strength distribution found by fracturing the test pieces 10 which survived an evaluation test wherein a bending stress corresponding to 100% of the average strength (the relative stress is 1) was applied at the first momentary loading. Plots with a symbol of "△", plots with a symbol "▽" and plots with a symbol of "◇" designate the survived test pieces 10 and the fractured test pieces 10 after the first, the second and the third (constant stress) loading of bending stresses, respectively. Thick vertical lines designate stresses applied in the test, and the test pieces plotted on the thick vertical lines are ones which survived at each loading.

As seen from FIG. 4, the gradient of the strength distribution of the survived test pieces 10 (plotted with the symbol "□") is definitely steeper (variation is small) than the gradient of the strength distribution of the test pieces 10 before the evaluation test (plotted with the symbol "○"). This means that test pieces which had required strength could be surely selected from the group of brittle material test pieces which had a great variation in strength. The lowest strength of the test pieces 10 after the evaluation test was 95% of the average strength of the test pieces before the evaluation test, showing that the test pieces 10 which survived the evaluation test had almost no tendency of strength degradation.

This means not only that the test pieces 10 which caused strength degradation by the first momentary loading could be surely eliminated by the subsequent stress applications, but also that there was almost no strength degradation due to the subsequent stress applications. In the stress application pattern stated above, about half of the test pieces 10 were fractured because the peak load value of the first momentary loading was set to the average strength of the test pieces 10. The peak load value of the first momentary loading is determined, depending on to what extent strength proof is required, in other words, under what conditions brittle material pieces are used. If proof strength can be lowered, the peak load value of the first momentary loading can be lessened to increase the yield of survived pieces.

Now, the test results of the strength evaluation method of the present invention which was carried out with the stress loading pattern stated above will be compared with a test results of a conventional strength evaluation method for a brittle material.

Figure 3:
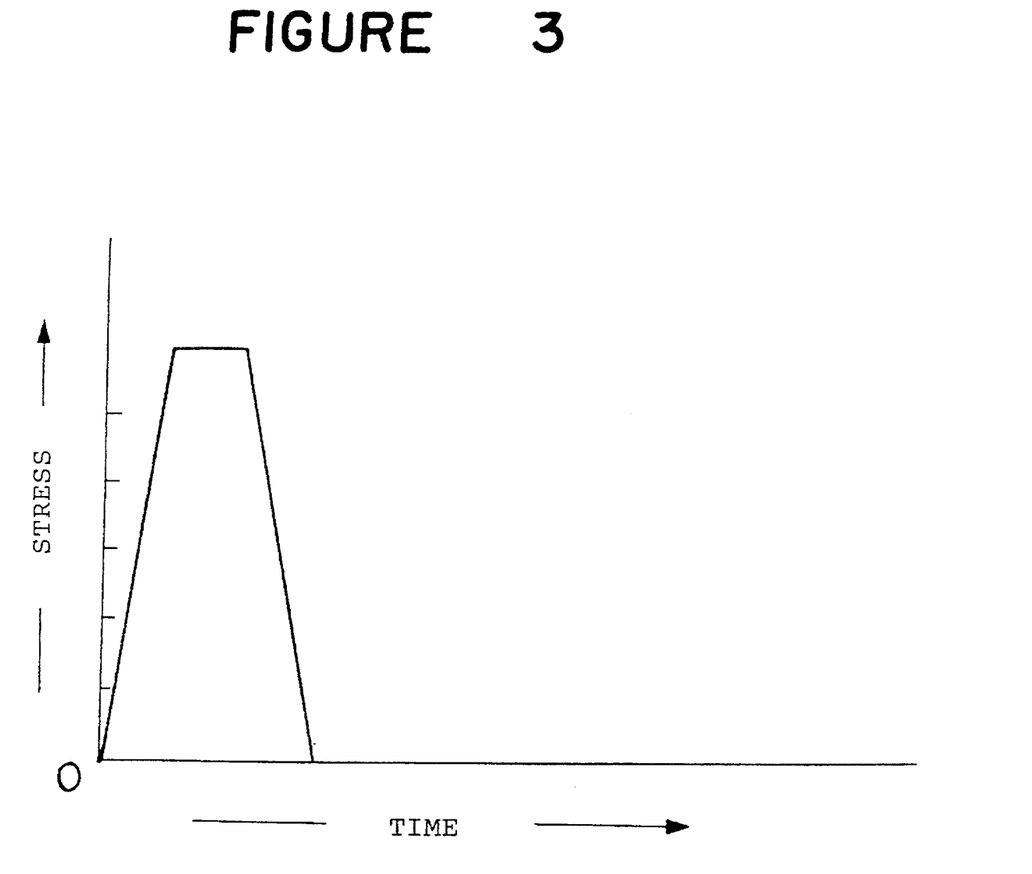
FIG. 3 is a stress application pattern diagram showing an example of the application pattern of a stress applied in a conventional strength evaluation method for a brittle material piece.

In FIG. 3, there is shown a stress application pattern in the conventional strength evaluation method which was applied to a similar three point bending strength test. A stress which corresponded to 90% of the average strength of tested pieces 10 (42 pieces) was applied at a loading edge speed of 0.5 mm/min, was held for 1 sec, and was released at the same edge speed. The test pieces 10 which had survived the evaluation test were fractured at a loading edge speed of 0.5 mm/min to measure the strength of the survived pieces, and obtained the strength distribution of the survived pieces 10.

Figure 5:
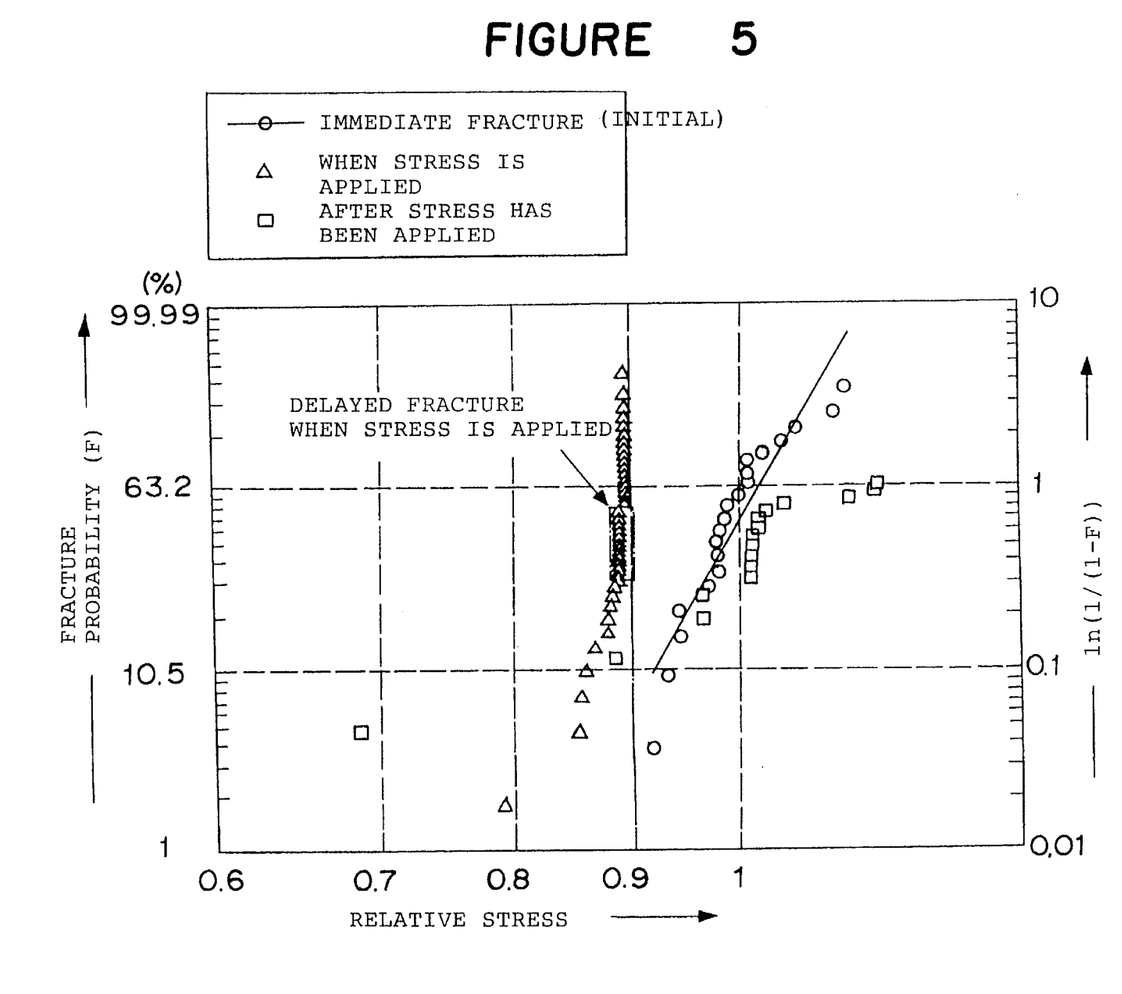
FIG. 5 is a Weibull strength distribution diagram of the fracture strength of brittle material pieces showing an example of the test results in accordance with the conventional strength evaluation method for brittle material pieces.

In FIG. 5, there are shown the test results in accordance with the conventional strength evaluation method. In FIG. 5, plots with a symbol "○" designate the initial Weibull strength distribution of the test pieces 10 before the test. Plots with a symbol of "□" designate the Weibull strength distribution of the test pieces 10 which were not fractured by the evaluation test with a stress of 90% of the average strength (the relative stress is 0.90) applied. Plots with a symbol "△" designate the survived test pieces 10 and the fractured test pieces 10 after the stress application. A thick vertical line designate a tensile stress applied in the test, and the test pieces plotted on the thick vertical line are ones which have not fractured.

As seen from FIG. 5, the gradient of the Weibull strength distribution of the survived test pieces 10 after the evaluation test is gentler (variation is great) than that of the Weibull strength distribution of the test pieces 10 before the evaluation test, showing that the evaluation test degraded the strength distribution. This means not only that the test pieces 10 which had required strength were not effectively selected from the group of brittle material test pieces 10 having a variation in strength, and no effective evaluation test was carried out, but also that the evaluation test caused significant strength degradation.

In accordance with the conventional strength evaluation method wherein the bending stress was applied at a loading edge speed (0.5 mm/min), was held at a predetermined stress for 1 sec, and the stress was released with the same edge speed, ten test pieces 10 were fractured after reaching the predetermined stress, and significant delayed fracture behavior was found. In the conventional evaluation method, the time required for the applied stress to reach the predetermined stress from 85% of the predetermined stress was 1 sec, the time for holding at the predetermined stress was 1 sec, and the time required for the applied stress to be released from the predetermined stress to 85% of the predetermined stress was 1 sec, which means that it totally took 3 sec. It is concluded that strength degradation developed in the test pieces, and that such a long period of loading high stress caused the delayed fracture.

When the strength distribution of the survived test pieces 10 after the evaluation test was measured, two of the survived test pieces were fractured at a lower stress than the stress applied in the evaluation test. In particular, the strength in one of them lowered to not higher than 70% of the average strength, causing significant strength degradation. According to the results shown in FIG. 5, it is assumed that each strength of the test pieces 10 without strength degradation in the evaluation test (the initial strength found with respect to the fracture probability by excluding fractured 22 test prices from totally 42 test pieces is above about 1.0 (the relative strength 1.0 corresponds to the initial average strength, the same definition will be applied later on). This means that when the applied stress was set to be 0.9 of the relative strength, strength degradation due to the stress application extended even to test pieces which had higher strength by 10% or more.

As explained, in accordance with the strength evaluation method of the present invention, the Weibull strength distribution of the survived test pieces after the evaluation test can be significantly improved in comparison with the conventional strength evaluation method. According to the present invention, products which have required strength can be surely selected from a group of brittle materials which have a wide variation in strength.

Now, preferable setting of the stress value in the second momentary loading and its subsequent momentary loading in accordance with the strength evaluation method of the present invention will be described. It is important to what extent the applied stress in the second momentary loading is decreased with reference to the applied stress in the first momentary loading. It is necessary to set the extent of decrease so that most of the survived test pieces in the first momentary loading can survive without being subjected to strength degradation at the second momentary loading.

It is preferable that a preliminary test is carried out to determine the stress value in the second momentary loading and its subsequent momentary loading. In detail, an another group of test pieces for the preliminary test which are of same material with the test pieces to be evaluated are subjected to a first momentary loading in advance. The Weibull strength distribution of the test pieces which have survived at the first momentary loading is obtained. A stress which corresponds to desired fracture probability based on the Weibull strength distribution is set as the stress value for the second momentary loading. For example, when the stress value for the second momentary loading is set to 85% of the stress value for the first momentary loading, and the stress value for the third momentary loading is set to 72% of the stress value for the first momentary loading (=85% of the first loading stress×85% of the second loading stress), the final fracture probability with respect to the final stress value of the survived piece to which a plurality of momentary loading is applied is represented by the product of fracture probability in each momentary loading.

For example, if the fracture probability of the pieces for each momentary loading is 1/100 (1%) (see FIG. 4 about the relationship between the fracture probability and the applied stress), the fracture probability of the survived test pieces after the final stress application in three momentary loading can be decreased to $(1/100)^3 = 1/1000000$. It shows that the surviving probability of the finally survived brittle material pieces with respect to the finally applied loading can drastically increased by repeating the momentary stress loading a plurality of times so that the peak load value of the momentary loading is gradually decreased.

Figure 6:
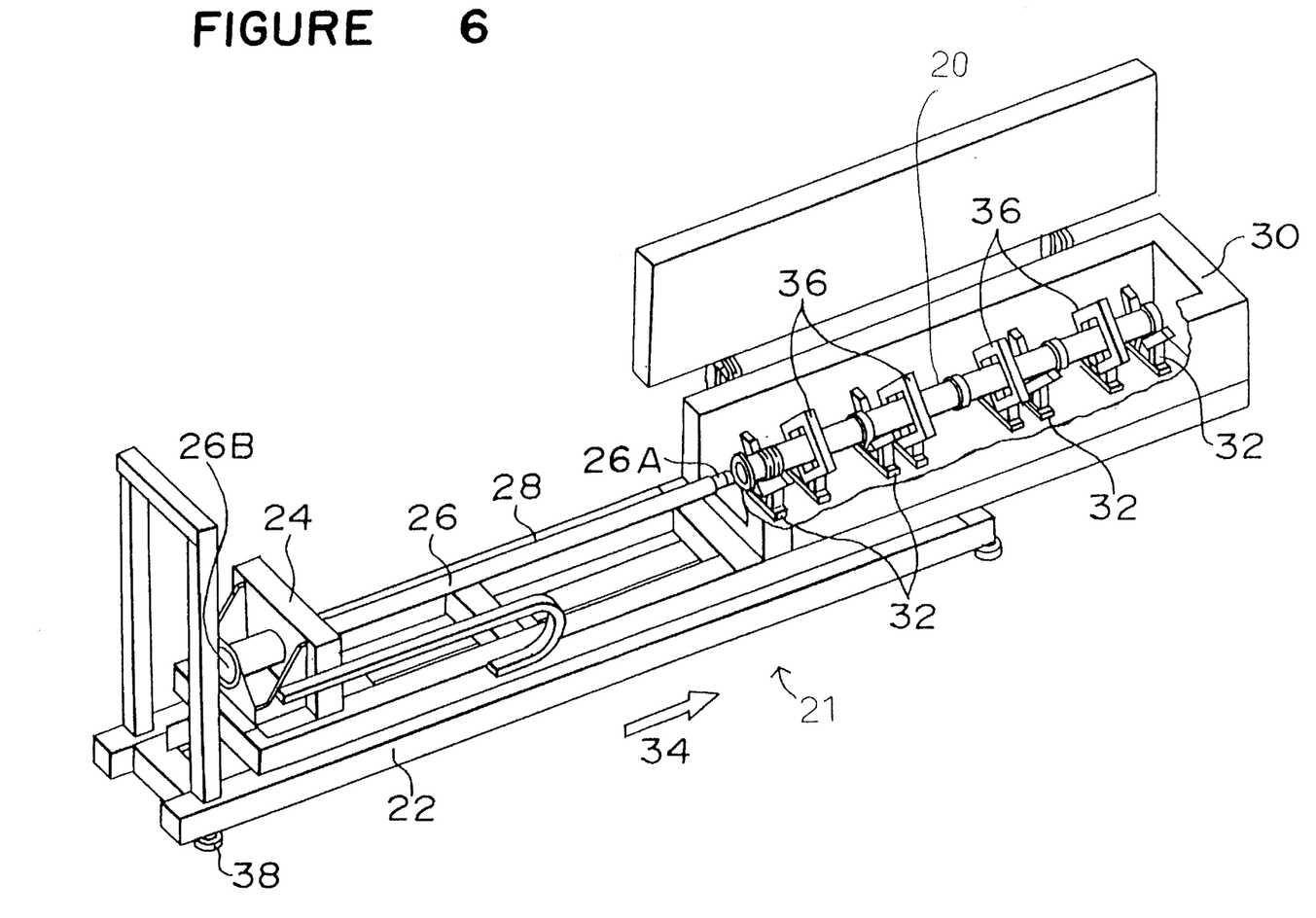
FIG. 6 is a schematic view showing an embodiment of an evaluation testing apparatus for filter tubes of the present invention.
Figure 7:
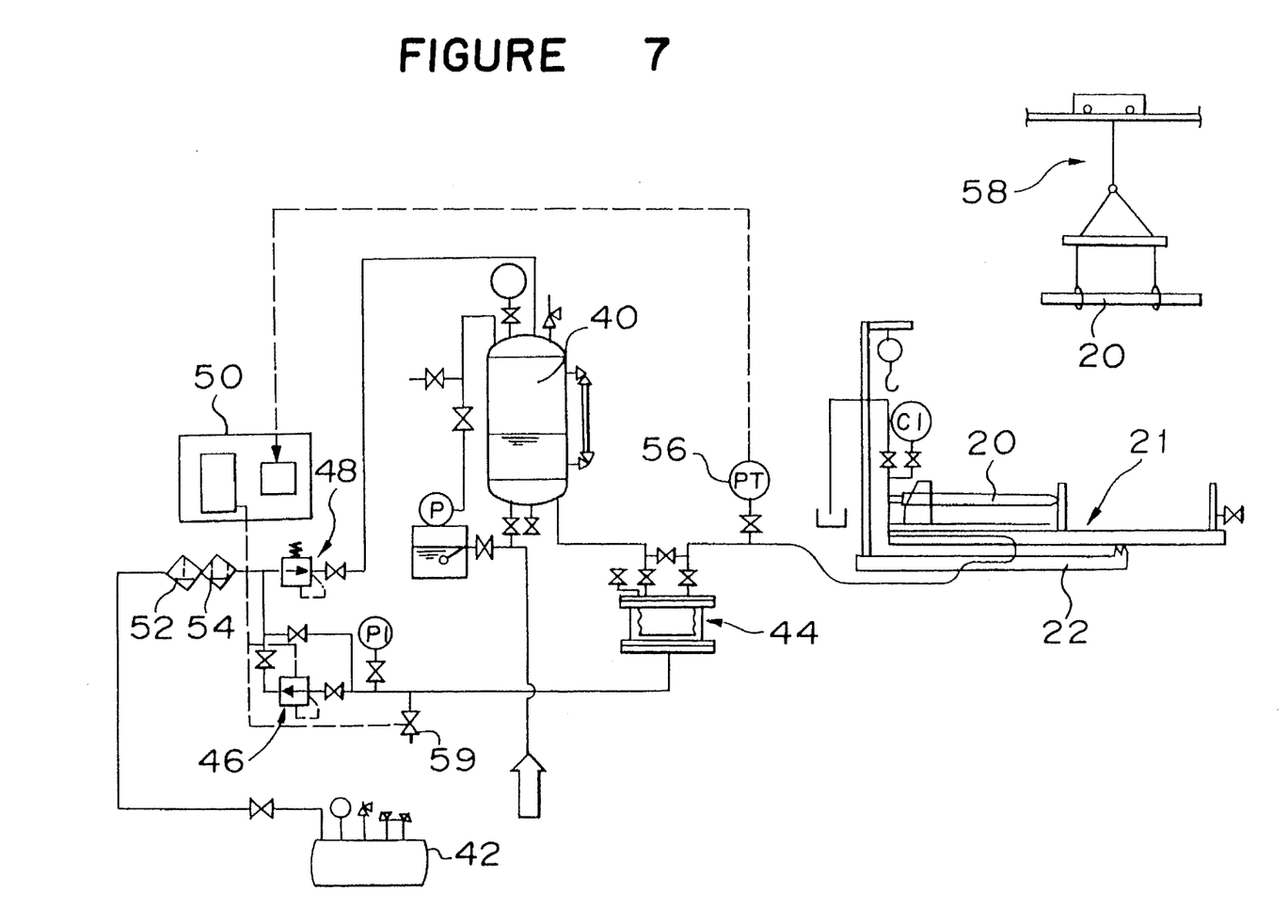
FIG. 7 is a piping diagram showing an example of the piping in the evaluation testing apparatus for filter tubes of the present invention.

Now, an example wherein the strength evaluation method according to the present invention is applied to porous ceramics filter tubes which are used in a filter apparatus for filtering hot gas including dust will be explained. In FIG. 6, there is shown a schematic view of an evaluation test apparatus 21 wherein the strength evaluation method according to the present invention is applied to a filter tube 20. In FIG. 7, there is shown a piping diagram in the evaluation test apparatus. As shown in FIG. 6, a supporting plate 24 which is mounted slidable on a rectangular base frame 22 supports a feeding pipe 26 in a cantilever fashion to arrange the feeding pipe in parallel with the longitudinal direction of the base frame 22. The feeding pipe 26 has a front edge 26A closed and a rear edge formed with an opening 26B for introducing pressurized water. The feeding pipe 26 has a circumferential surface formed with many apertures (not shown). The feeding pipe 26 has an elastomer sleeve (hollow elastomer) 28 with one end opened mounted thereon from the front edge 26A to the vicinity of the opening 26B at the rear edge to apply a pressure.

The filter tube 20 (the filter tube made of cordierite and having an entire length of about 2400 mm) to be subjected to the evaluation test has the elastomer sleeve 28 inserted therein. The filter tube 20 is supported by a plurality of holders 32 which are arranged in a sound insulated case 30 on the base frame 22. When the evaluation test is carried out to the filter tube 20, the supporting plate 24 is slid in a direction of an arrow 34 to set the elastomer sleeve 28 at a predetermined position. Next, water is introduced from the rear end opening 26B of the feeding pipe 26 into the feeding pipe, the pressurized water flows from the apertures on the circumferential surface of the feeding pipe to expand the elastomer sleeve 28 equally, thereby to apply an internal pressure from the inside of the filter tube 20 (apply a tensile stress to the filter tube in a circumferential direction).

A plurality of AE sensors 36 for detecting acoustic emission are arranged in the vicinity of the holders 32 for supporting the filter tube 20 to monitor the advancement of strength degradation during the evaluation test. The AE sensors 36 detect elastic waves (acoustic emission) accompanied by the growth or the deformation of a crack caused in the material when a tensile stress is applied to the material. Since external noise has to be excluded to the utmost in order to detect the acoustic emission by the AE sensors 36, the sound insulated case 30 is provided to enclose the filter tube. In addition, in order to prevent vibration from occurring in the evaluation test, vibration proofing mounts 38 are attached at the four corners below the base frame 22.

In the evaluation test system shown in the piping diagram of FIG. 7, firstly, water is directly introduced from a feed water tank 40 into the elastomer sleeve 28 to fill the elastomer sleeve 28 with water, and then a bellows pump 44 is operated by the compressed air from a compressor 42 to carry out pressurized water introduction. In the momentary loading wherein loading is applied momentarily, a regulator 46 for compressed air is fully opened for an abrupt raise in pressure up to a set maximum water pressure of n kgf/cm$^2$, and a pressure reducing valve 48 is opened for an abrupt decrease in pressure (the stress loading is released) at the instant when the set water pressure (the set applied stress) is reached. As a result, the loading application can be increased to n kgf/cm$^2$ in 2 sec or less, and after that the loading application can be decreased in 0.5 sec or less to zero kgf/cm$^2$ which means no loading state. In order to effectively carry out the evaluation test for several hundreds of filter tubes 20, a sequence of water introducing operation, pressure increasing operation, pressure decreasing operation and drainage operation have been carried out in a semiautomatic manner. In FIG. 7, reference numeral 50 designates a controller, reference numeral 52 designates an air filter, reference numeral 54 designates a mist separator, reference numeral 56 designates a pressure transmitter and reference numeral 58 is a crane for hoisting the filter tube 20.

The evaluation test apparatus 21 for a filter tube constructed as mentioned above was used to conduct an evaluation test for filter tubes in accordance with the stress loading pattern shown in FIG. 2. In the evaluation test, filter tubes 20 which were fractured by two times of momentary loading and four times of constant stress loading were excluded. In addition, when the constant stress loading was exerted four times, the AE sensors 36 were used to estimate to what extent the strength degradation in each filter advanced. The estimation was made based on how the acoustic emission which occurred at the time of increasing the loading attenuated. In this way, a few of filter tubes were determined to be defective ones even if they did not fracture.

The results of the evaluation test show that filter tubes which had required strength could be surely selected from a group of the filter tubes which had a wide variation in strength as shown in the results of the evaluation test on the test pieces in the above-mentioned bending strength test. In addition, the surviving probability of the evaluated filter tubes which finally passed the test could be drastically raised.

Although explanation on this embodiment was made for the case wherein a combination of two times of momentary loading and four times of constant stress loading was applied, the application of the constant stress loading can be omitted depending on the minimum surviving probability.

As described above, in accordance with the strength evaluation method of the present invention, the momentary loading wherein a tensile stress is momentarily applied to a brittle material is repeated a plurality of times, and the peak load value of the subsequent momentary loading is gradually decreased. As a result, it is possible to accurately evaluate the strength of the brittle material pieces while minimizing occurrence of strength degradation in the brittle material pieces, and to select the brittle material pieces which have a small variation in strength.

In addition, it is possible not only to surely select brittle material pieces having desired proof strength from a group of brittle material pieces having a wide variation in strength, but also to drastically increase the surviving probability of the brittle material pieces that passed the test finally.

Further, the application of momentary loading is hardly susceptible to cause strength degradation in brittle material pieces even if a stress equivalent to the average strength of the brittle material pieces is applied to the brittle material pieces. As a result, the yield of survived pieces in an evaluation test can be increased.

Obviously, numerous modifications and variations of the present invention are possible in light of the above teachings. It is therefore to be understood that within the scope of the appended claims, the invention may be practiced otherwise than as specifically described herein.

What is claimed is:

1. A strength evaluation method for evaluating the strength of brittle material pieces by applying a stress, the method comprising the steps of:

repeating momentary loading a plurality of times to a brittle material piece, the momentary loading momentarily applying a tensile stress to the brittle material piece and then immediately releasing the tensile stress; and gradually decreasing a peak load value of a subsequent momentary loading of said repeated momentary loadings.

2. A strength evaluation method according to claim 1, further comprising applying a constant stress loading at least one time after a final momentary loading of said repeated momentary loadings, the constant stress loading applying for a predetermined period of time a tensile stress which has smaller value than the peak load value of the final momentary loading.

3. A strength evaluation method according to claim 1, wherein the peak load value of the tensile stress at a subsequent momentary loading of said repeated momentary loadings is set to a proof strength of a group of brittle material pieces to be evaluated.

4. A strength evaluation method according to claim 1, wherein the peak load value of the tensile stress at a subsequent momentary loading of said repeated momentary loadings is set to a tensile stress which corresponds to a desired fracture probability in advance based on a Weibull strength distribution, and wherein the Weibull strength distribution is obtained by seeking a strength distribution of a group of brittle material pieces which are not fractured by the momentary loading just before, and processing the sought strength distribution according to Weibull statistical analysis.

5. A strength evaluation method according to claim 1, wherein the brittle material is a heterogeneous material.

6. A strength evaluation method according to claim 5, wherein the brittle material is a ceramics or a product made thereof.

7. A strength evaluation method according to claim 5, wherein the brittle material is a porous material.

8. A strength evaluation method according to claim 1, wherein the brittle material piece is a tube, and a hollow elastomer is arranged in the tube, the method comprising the further step of introducing a fluid into the hollow elastomer to expand the hollow elastomer, thereby applying a tensile stress to the tube in a circumferential direction.

* * * * *